(12) United States Patent
Luo et al.

(10) Patent No.: US 12,390,192 B2
(45) Date of Patent: Aug. 19, 2025

(54) DETECTION PROBE, TRANSMISSION APPARATUS, AND DETECTION DEVICE

(71) Applicant: EDAN INSTRUMENTS, INC., Shenzhen (CN)

(72) Inventors: Hua Luo, Shenzhen (CN); Qi Ma, Shenzhen (CN); Dan Zhou, Shenzhen (CN); Bo Ouyang, Shenzhen (CN); Jianhua Mo, Shenzhen (CN)

(73) Assignee: EDAN INSTRUMENTS, INC., Shenzhen (CN)

( * ) Notice: Subject to any disclaimer, the term of this patent is extended or adjusted under 35 U.S.C. 154(b) by 82 days.

(21) Appl. No.: 18/472,262

(22) Filed: Sep. 22, 2023

(65) Prior Publication Data

US 2024/0023935 A1 Jan. 25, 2024

Related U.S. Application Data (63) Continuation of application No. PCT/CN2021/082439, filed on Mar. 23, 2021.

(51) Int. Cl.
*A61B 8/00* (2006.01)
*G01S 7/52* (2006.01)
*A61B 8/12* (2006.01)

(52) U.S. Cl.
CPC ........ *A61B 8/4461* (2013.01); *G01S 7/52079* (2013.01); *A61B 8/12* (2013.01)

(58) Field of Classification Search
None
See application file for complete search history.

(56) References Cited

U.S. PATENT DOCUMENTS

| | | |
|---|---|---|
| 5,450,851 A | 9/1995 | Hancock |
| 2006/0173330 A1 | 8/2006 | Kim |

(Continued)

FOREIGN PATENT DOCUMENTS

| | | |
|---|---|---|
| CN | 102018531 A | 4/2011 |
| CN | 103006262 A | 4/2013 |

(Continued)

OTHER PUBLICATIONS

International Search Report, International Application No. PCT/CN2021/082439, mailed Dec. 28, 2021 (18 pages).

(Continued)

*Primary Examiner* — Shahdeep Mohammed (57) ABSTRACT

A detection probe, a transmission apparatus, and a detection device are provided. The detection probe includes a housing, a detection mechanism, a driving mechanism, and a rope transmission mechanism. The housing defines an accommodation space. The detection mechanism is arranged on one end of the housing, and is configured to perform a detection function. The driving mechanism is arranged in the accommodation space, and is configured to output a force. The rope transmission mechanism is arranged in the accommodation space, and includes a rope set and a tension member. One end of the rope set is connected to the driving mechanism, and other end of the rope set is connected to the detection mechanism. The tension member is connected to the rope set, and is configured to apply a force to one end of the rope set away from the detection mechanism.

20 Claims, 6 Drawing Sheets

(56) References Cited

U.S. PATENT DOCUMENTS

| | | | |
|---|---|---|---|
| 2007/0016060 A1 | 1/2007 | Hwang | |
| 2013/0172751 A1* | 7/2013 | Heinrich | G10K 11/004 |
| | | | 600/447 |
| 2014/0036634 A1 | 2/2014 | Tang | |

FOREIGN PATENT DOCUMENTS

| | | |
|---|---|---|
| CN | 104224228 A | 12/2014 |
| CN | 105662461 A | 6/2016 |

OTHER PUBLICATIONS

European Search Report, European Application No. 21932081.9, mailed Mar. 7, 2024 (8 pages).

* cited by examiner

DETECTION PROBE, TRANSMISSION APPARATUS, AND DETECTION DEVICE

CROSS REFERENCE TO RELATED APPLICATIONS

The present disclosure is a continuation of International Patent Application No. PCT/CN2021/082439, filed Mar. 23, 2021, the contents of which is herein incorporated by reference in its entirety.

TECHNICAL FIELD

The present disclosure relates to the field of medical devices, in particular to a detection probe, a transmission apparatus, and a detection device.

BACKGROUND

A detection probe for medical detection, such as an ultrasonic probe, is capable of transmitting an ultrasonic signal for detection through an acoustic head assembly, receiving an ultrasonic signal including detection information, and acquiring a detection result by analysis.

In a practical application, in order to improve an accuracy and a comprehensiveness of the detection result, different parts may be detected by driving the acoustic head assembly to swing. However, due to factors such as limitations of a structure and a space of the detection probe, requirements for a transmission mechanism configured to transmit a driving force to the acoustic head assembly are increasingly high.

SUMMARY

In order to solve the above problem, a solution of the present disclosure is to provide a detection probe. The detection probe includes a housing, a detection mechanism, a driving mechanism, and a rope transmission mechanism. The housing defines an accommodation space. The detection mechanism is arranged on one end of the housing, and is configured to perform a detection function. The driving mechanism is arranged in the accommodation space, and is configured to output a force. The rope transmission mechanism is arranged in the accommodation space, and includes a rope set and a tension member. One end of the rope set is connected to the driving mechanism, and other end of the rope set is connected to the detection mechanism. The rope set is configured to receive the force output by the driving mechanism, transmit the force to the detection mechanism, and drive the detection mechanism to move. The tension member is connected to the rope set, is configured to apply a force to one end of the rope set away from the detection mechanism and enable the rope set to be in a tension state.

In order to solve the above problem, a solution of the present disclosure is to provide a transmission apparatus. The transmission apparatus is arranged in a detection probe including a detection mechanism and a driving mechanism. The transmission apparatus includes a rope set and a tension member. One end of the rope set is connected to the driving mechanism, and other end of the rope set is connected to the detection mechanism. The rope set is configured to receive a force output by the driving mechanism, transmit the force to the detection mechanism, and drive the detection mechanism to move. The tension member is connected to the rope set, is configured to apply a force to an end of the rope set away from the detection mechanism and enable the rope set to be in a tension state.

In order to solve the above problem, a solution of the present disclosure is to provide a detection device. The detection device includes a host and the detection probe mentioned above. The host is connected to a detection mechanism and a driving mechanism of the detection probe, configured to control the driving mechanism to output a force and control the detection mechanism to perform a detection function.

BRIEF DESCRIPTION OF THE DRAWINGS

In order to make technical solutions described in some embodiments of the present disclosure or in the related art more clearly, the drawings used for description of some embodiments or the related art will be described. Apparently, the drawings in the following description only illustrate some embodiments of the present disclosure. For those skilled in the art, other drawings may be acquired according to the drawings without any creative work.

DETAILED DESCRIPTION

In order to make the object, the technical solutions and the technical effect of the present disclosure more clearly, the present disclosure is further explained in detail below in combination with the drawings and some embodiments. It should be understood that some embodiments described in the description are only for a purpose of interpreting the present disclosure and not for a purpose of limiting the present disclosure. Without conflict, an embodiment or a feature of the present disclosure may be combined with some other embodiments of the present disclosure and/or some other features.

Some embodiments of the present disclosure provide a detection device configured to detect a body surface and/or an internal body tissue to acquire a detection result. In some application scenarios, the detection device may also be configured to detect an animal, which is not limited.

Figure 1:
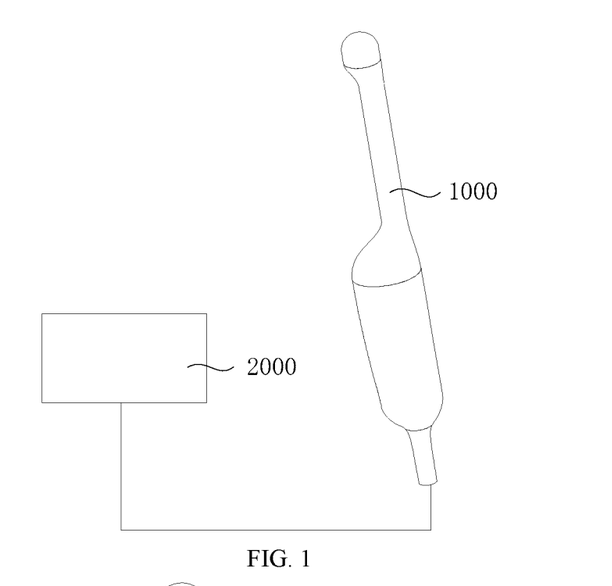
FIG. 1 is a structural schematic view of a detection device according to some embodiments of the present disclosure.

As shown in FIG. 1, in some embodiments, the detection device may include a detection probe 1000 and a host 2000. The detection probe 1000 may be connected to the host 2000 in a wired or wireless manner, thereby detecting a to-be-detected part of a human body under a control of the host 2000.

The detection probe 1000 may be a 3-dimensional (D) mechanical probe, a 4-D mechanical probe, or the like, i.e., an ultrasonic probe having a 3-D/4-D imaging function. Under a control signal of the host 2000, the detection probe 1000 transmits an ultrasonic signal to the human body tissue and receives an echo signal carrying human body tissue information. The host 2000 images the human body tissue by processing the echo signal of the detection probe 1000, such that a 3-D/4-D image of the human body tissue is constructed for medical analysis. For example, a gynecological examination or the like may be performed by the 3-D/4-D mechanical probe.

The detection probe 1000 may also be configured for other purposes, such as transmitting electrical stimulation to human tissues, performing physical massage, or the like under the control signal of the host 2000, which are not limited.

Figure 2:
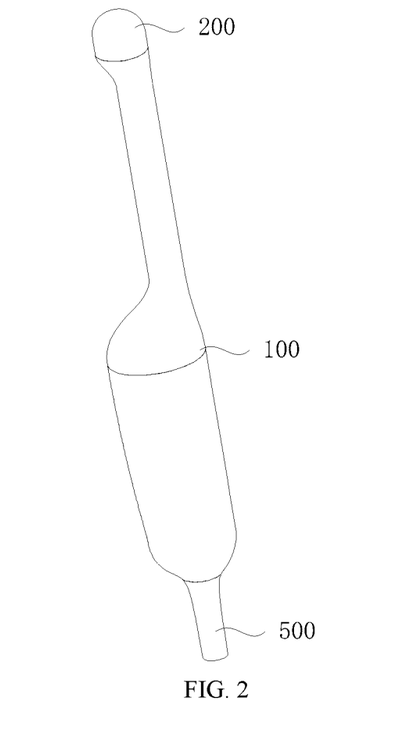
FIG. 2 is a structural schematic view of a detection probe according to some embodiments of the present disclosure.
Figure 3:
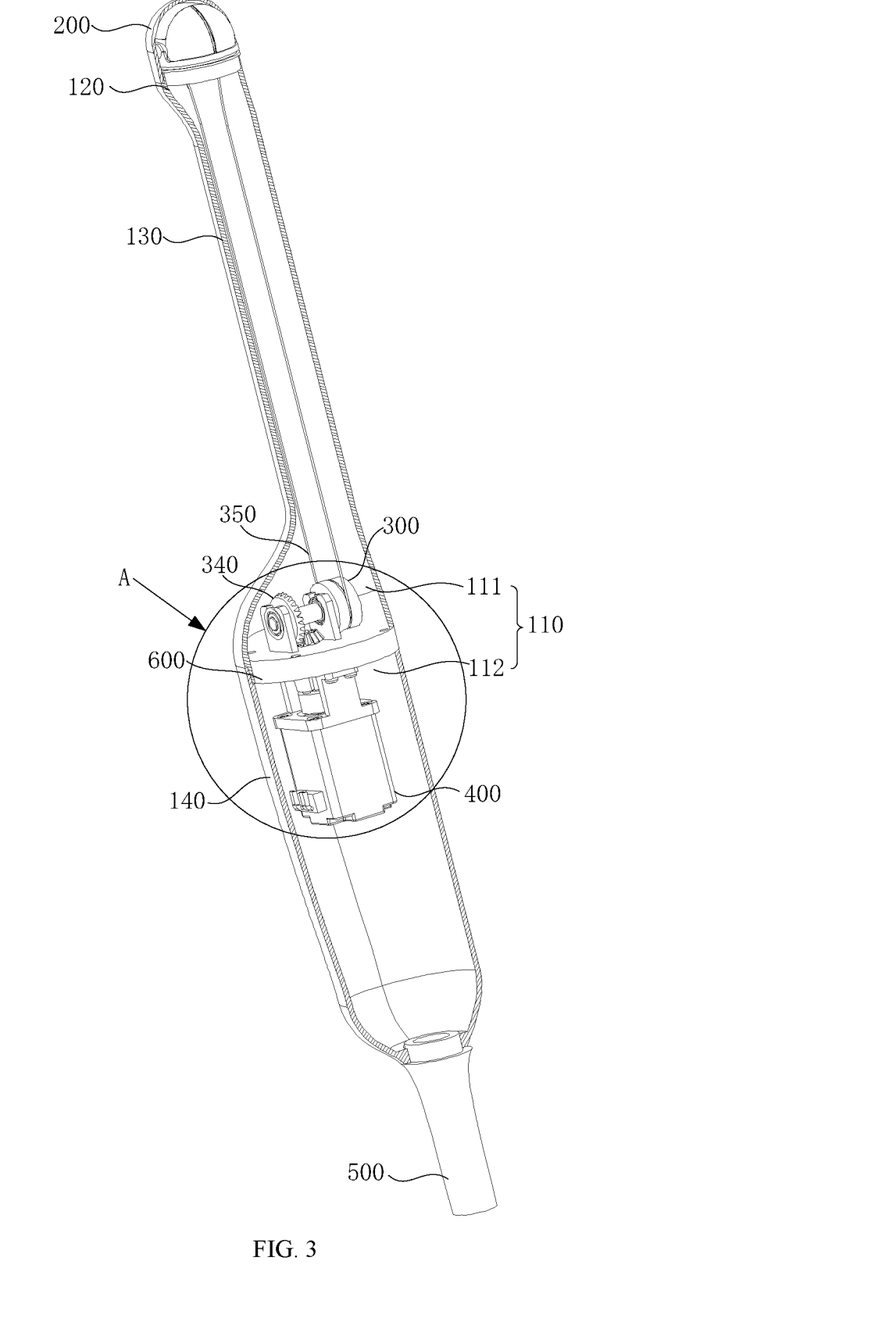
FIG. 3 is a structural schematic view of a partial detection probe according to some embodiments of the present disclosure.

In some embodiments, as shown in FIGS. 2 and 3, the detection probe 1000 may include a housing 100, a detection mechanism 200, a transmission apparatus 300, a driving mechanism 400, a tail sleeve assembly 500, a mounting assembly 600, and the like. The transmission apparatus 300 may be connected to the driving mechanism 400 and the detection mechanism 200. The host 2000 may be connected to the driving mechanism 400 and the detection mechanism 200 through the tail sleeve assembly 500, and may control operation of the driving mechanism 400 to drive the transmission apparatus 300 to drive the detection mechanism 200 to move. The detection mechanism 200 may feed back detected information to the host 2000 for analysis and processing to acquire a detection result.

In some embodiments, the detection probe 1000 may include more or less structures than the above structures, which may be selected according to a practical need, and are not limited.

The housing 100 defines an accommodation space 110, and one end of the housing 100 has an opening 120 in communication with the accommodation space 110. The accommodation space 110 is configured to accommodate at least partially internal structure of the detection probe 1000 to support and protect the internal structure.

The housing 100 may be a one-piece structure or may be separately assembled from a plurality of different parts. In some embodiments, the housing 100 may include an insertion portion 130 and a holding portion 140, which are connected to each other to jointly form the housing 100. The insertion portion 130 and the holding portion 140 may be connected to each other through at least one of adhesive bonding, clamping, or buckling, etc., which is not limited.

Correspondingly, the insertion portion 130 and the holding portion 140 may correspond to an extension region 111 and an accommodation region 112 of the accommodation space 110 respectively, and the transmission apparatus 300 and the driving mechanism 400 may be accommodated in the extension region 111 and the accommodation region 112 respectively. It should be noted that, in some embodiments of the present disclosure, a corresponding relationship between each region of the accommodation space 110 and each functional mechanism is not limited. For example, in some application scenarios, a part of the transmission apparatus 300 may be accommodated in the extension region 111, and other part of the transmission apparatus 300 may be accommodated in the accommodation region 112, which may be configured according to a practical situation.

In some embodiments, a shape, a size, and the like of each part of the housing 100 may be determined according to its function, a shape, a size, and a function of an internal structure accommodated in a corresponding region of the accommodation space 110.

It should be noted that the detection probe 1000 in some embodiments may be inserted into the human body to detect internal tissues of the human body. In a practical operation, the detection mechanism 200 is located at a "head". An operator holds the holding portion 140, and inserts the detection mechanism 200 into the body to perform the detection function through an extension of the insertion portion 130, and the tail sleeve assembly 500 is located outside the human body, so as to facilitate each functional mechanism corresponding each part of the detection probe 1000 to perform a corresponding function.

Figure 4:
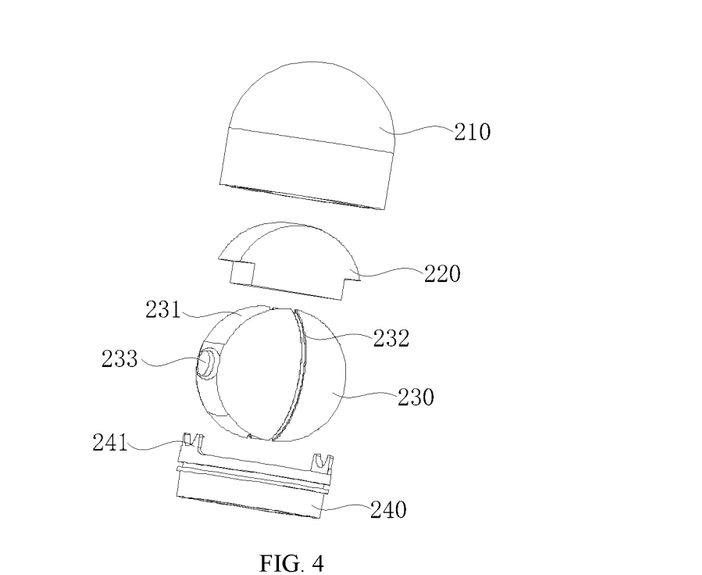
FIG. 4 is an explosive structural schematic view of a detection mechanism of a detection probe according to some embodiments of the present disclosure.

In some embodiments, as shown in FIG. 4, the detection mechanism 200 may include an acoustic window 210, an energy conversion element 220, a mounting base 230, and a supporting bracket 240.

The energy conversion element 220 may establish a connection relationship with the host 2000, transmit an ultrasonic wave served as a detection signal to a to-be-detected tissue of the human body according to the control signal transmitted by the host 2000, and receive a feedback signal carrying detection information.

The acoustic window 210 may have a property of letting acoustic wave pass through, and may be arranged at a periphery of the energy conversion element 220. In some embodiments, the acoustic window 21 may be arranged at the opening 120 at one end of the housing 100, and may wrap and be arranged outside the energy conversion element 220, the mounting base 230, and the supporting bracket 240. It should be noted that, in a practical application, coupling liquid for ultrasonic transmission may be filled between the acoustic window 210 and the energy conversion element 220, so as to transmit an ultrasonic wave detection signal and receive a feedback signal through a cooperation of the energy conversion element 220, the coupling liquid and the acoustic window 210.

The mounting base 230 defines an assembly position 231 configured to accommodate the energy conversion element 220 to assemble the energy conversion element 220 on the mounting base 230. In some embodiments, the energy conversion element 220 may be attached to the assembly position 231 by an adhesive, such as an epoxy adhesive. In addition, assembly grooves 232 may be defined on two side of the mounting base 230, and may be configured to assemble some components of the transmission apparatus 300, so as to connect to the transmission apparatus 300.

The supporting bracket 240 may be configured to support the mounting base 230, thereby supporting the energy conversion element 220. In some embodiments, the supporting bracket 240 may be in a shape of annular, such as a circular ring, a square ring, or the like. The shape of the supporting bracket 240 may match a shape of an inner wall of the housing 100 at the opening 120, and may be arranged on the inner wall of the housing 100 at the opening 120.

The supporting bracket 240 may include two concave arc supporting platforms 241 having concave arc supporting surfaces. In some embodiments, the mounting base 230 may also have two cylindrical protrusions 233 arranged on two sides of the mounting base 230 respectively, and the cylindrical protrusions 233 may have arc side surfaces respectively configured to be movably supported on corresponding concave arc supporting surfaces of the supporting bracket 240, such that the mounting base 230 may swing under the support of the concave arc supporting platform 241. In this way, in response to the mounting base 230 being subjected to a force applied by the drive device 300, the mounting base 230 may drive the energy conversion element 220 to perform reciprocating swing along certain directions.

Figure 5:
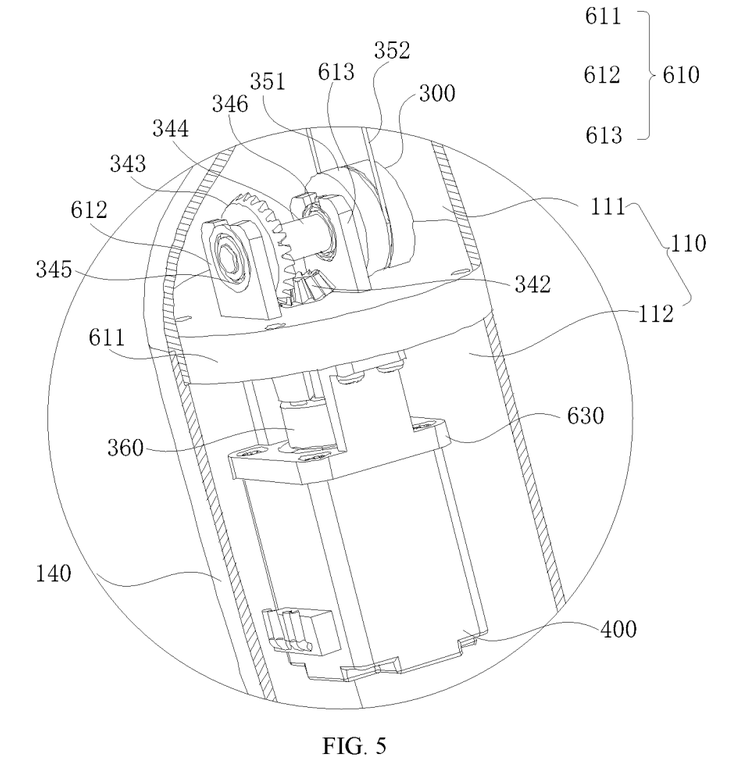
FIG. 5 is an enlarged structural schematic view of a part A shown in FIG. 3.
Figure 6:
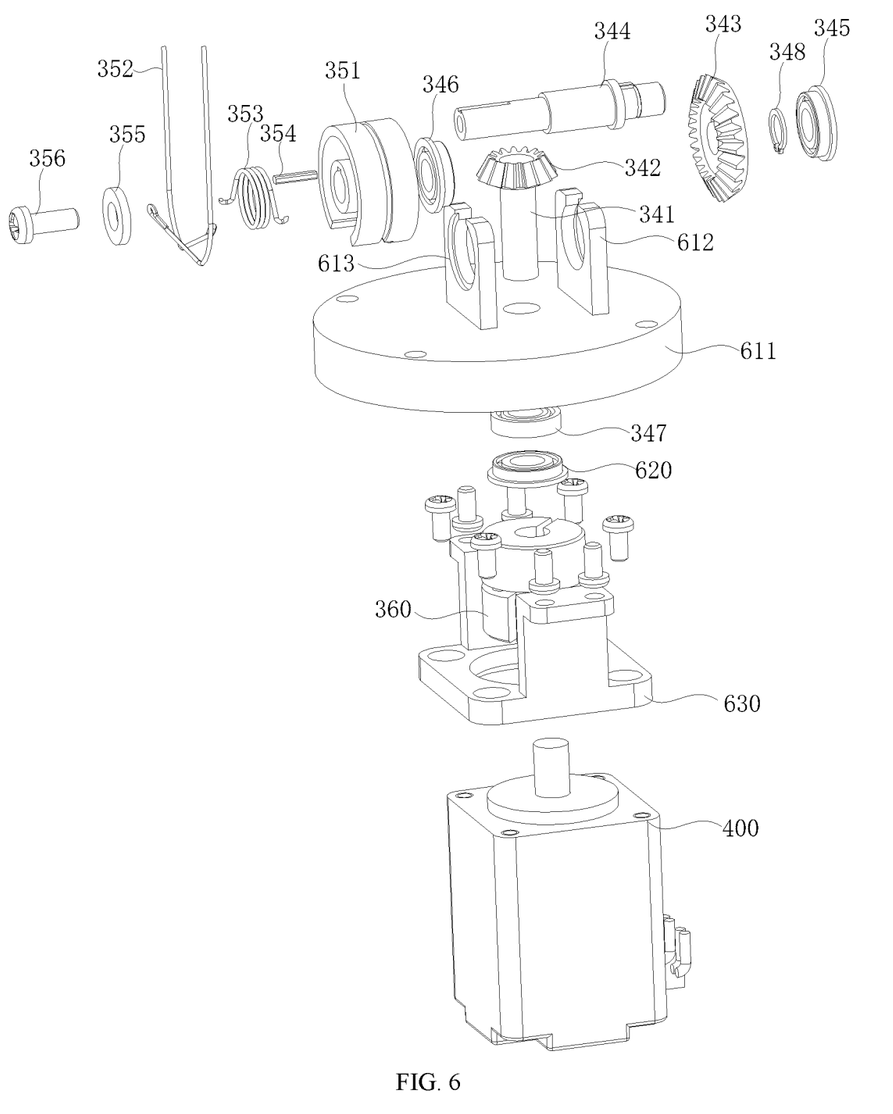
FIG. 6 is an explosive structural schematic view of a partial detection probe according to some embodiments of the present disclosure.

In some embodiments, as shown in FIGS. 3, 5 and 6, the transmission apparatus 300 may include a gear transmission mechanism 340, a rope transmission mechanism 350, and the like.

In some embodiments, the gear transmission mechanism 340 may be connected to the driving mechanism 400 and the rope transmission mechanism 350 to receive a force output by the driving mechanism 400 and transmit the force to the rope transmission mechanism 350. The rope transmission mechanism 350 is connected to the detection mechanism 200, and drives the detection mechanism 200 to move in response to the rope transmission mechanism 350 receiving the force transmitted by the gear transmission mechanism 340, thereby implementing a detection.

The transmission apparatus 300 may be arranged in the accommodation space 110 through the mounting assembly 600. In some embodiments, the transmission apparatus 30 may be arranged on the inner wall of the housing 100. In some embodiments, the mounting assembly 600 may include an assembly base 610, and the drive 300 may be arranged on the inner wall of the housing 100 through the assembly base 610.

Figure 7:
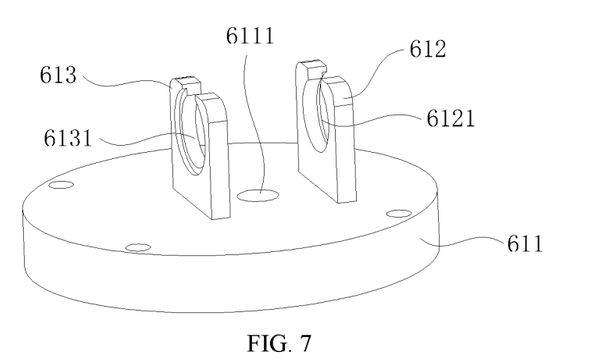
FIG. 7 is a structural schematic view of an assembly base of a detection probe according to some embodiments of the present disclosure.

In some embodiments, as shown in FIG. 7, the assembly base 610 may include an assembly base body 611, a first supporting bracket 612, and a second supporting bracket 613.

The assembly base body 611 may be arranged on the housing 100 and surrounded by the inner side wall of the housing 100. In some embodiments, the assembly base body 611 may be arranged on one end of the insertion portion 130 close to the holding portion 140, and may be arranged through adhesive bonding, clamping, interference fitting, or the like. In some embodiments, at least partial shape of the assembly base body 611 may also match the shape of the inner side wall of the housing 100 at an assembly location, such that a connection between the assembly base body 611 and the inner side wall of the housing 100 is hermetically sealed, thereby separating the extension region 111 of the accommodation space 110 from the accommodation region 112 of the accommodation space 110.

In some embodiments, the assembly base body 611 defines an assembly hole 6111 extending through the assembly base body 611, and the assembly base body 611 and the receiving areas 112 respectively arranged on two sides of the assembly base body 611 may be in communication with each other through the assembly hole 6111. The mounting assembly 600 may also include a seal member 620 arranged in the assembly hole 6111.

The first supporting bracket 612 and the second supporting bracket 613 are spaced apart from each other and arranged on two sides of the assembly holes 6111 respectively, are connected to one side of the assembly base body 611 facing the extension region 111, and defines a first assembly position 6121 and a second assembly position 6131 respectively.

The assembly base body 611, the first supporting bracket 612 and the second supporting bracket 613 may be independent structures respectively, and the first supporting bracket 612 and the second supporting bracket 613 may be arranged on the assembly base body 611 through bonding, clamping, screwing, or plugging, etc. In some embodiments, all or some of the assembly base body 611, the first supporting bracket 612, and the second supporting bracket 613 may also be a one-piece structure, which are not limited.

In some embodiments, the gear transmission mechanism 340 may include a driving shaft 341, a driving gear 342, a driven gear 343, a driven shaft 344, a first bearing 345, a second bearing 346, a third bearing 347, a fasten member 348, and the like.

One end of the driving shaft 341 is located on the extension region 111. Other end of the driving shaft 341 penetrates the assembly hole 6111 of the assembly base body 611, enters the accommodation region 112, and is connected to the driving mechanism 400.

In some embodiments, the transmission apparatus 300 may also include a shaft coupling 360. The other end of the driving shaft 341 may be connected to the shaft coupling 360 through the assembly hole 6111, and may be connected to an output end of the driving mechanism 400 through the shaft coupling 360, such that the driving mechanism 400 may drive the driving shaft 341 to rotate.

In some embodiments, the third bearing 347 may be sleeved on a periphery of the driving shaft 341 and arranged in the assembly hole 6111 to support a rotation of the driving shaft 341. The seal member 620 may be an oil seal, such as a framework oil seal or the like, and may be sleeved on the periphery of the driving shaft 341 and arranged in the assembly hole 6111 to seal the assembly hole 6111, thereby further separating the extension region 111 from the receptacle region 112.

The driving gear 342 is arranged on one end of the driving shaft 341 at the extension region 111 and rotates synchronously with the driving shaft 341 under a drive of the driving mechanism 400. It should be noted that the driving gear 342 and the driving shaft 341 may be independent structures, and may be connected together in a certain manner. In some embodiments, the driving shaft 341 and the driving gear 342 may also be a one-piece structure, that is, the driving shaft 341 and the driving gear 342 form a gear shaft, which may be selected according to a practical situation.

The driven gear 343 is engaged with the driving gear 342 and rotates with the driving gear 342. In a practical application, the driven gear 342 and the driving gear 343 with an appropriate number of teeth may be selected according to a need. For example, the number of teeth of the driven gear 343 may be greater than the number of teeth of the driving gear 342, such that a transmission ratio of the driving gear 342 to the driven gear 343 is greater than 1. In this way, a deceleration motion is implemented by gear transmission, thereby increasing the transmitted force to increase a torque for driving the energy conversion element 220 to swing. In addition, a driving mechanism having a larger output torque tends to have a larger volume and weight. However, the above arrangement of the gear transmission mechanism 340 may also increase the torque for driving energy conversion element 220 to swing without increasing the volume and weight of the driving mechanism 400, thereby improving a portability of the detection probe 1000.

It should be noted that the reciprocating swing of the energy conversion element 220 is driven by the driving mechanism 400. However, in some application scenarios, a drive direction of the output end of the driving mechanism 400 is inconsistent with the swinging direction required by the energy conversion element 220 due to factors such as structural and spatial limitations. Therefore, the transmission apparatus 300 may be designed to change a transmission direction of the force during a transmission, such that the transmission direction of the output end of the rope transmission mechanism 350 is consistent with the swinging direction required by the energy conversion element 220. In some embodiments, a structure configured to change the transmission direction may be arranged in the gear transmission mechanism 340, the rope transmission mechanism 350, or both of the gear transmission mechanism 340 and the rope transmission mechanism 350.

In some embodiments, the driving gear 342 rotates synchronously with the driving shaft 341 along a first direction under a drive of the driving mechanism 400, and the driven gear 343 rotates with the driving gear 342 along a second direction. In some embodiments, the driven shaft 344 is inserted in a center of the driven gear 343 and rotates synchronously with the driven gear 343 along the second direction.

In some embodiments, the gear transmission mechanism 340 may be arranged such that an axis of the driving shaft 341 and an axis of the driven shaft 344 form a preset angle which is greater than 0° and not greater than 90°. In other words, in this embodiment, the driving shaft 341 is not parallel to the driven shaft 344, such that the driven gear 343 changed the transmission direction from the first direction to the second direction under a drive of the driving gear 342.

In some embodiments, the output end of the driving mechanism 400 drives the driving shaft 341 to rotate in a direction perpendicular to the swinging direction required by the energy conversion element 220. In this case, the gear transmission mechanism 340 may be arranged such that the axis of the driving shaft 341 and the axis of the driven shaft 344 form a preset angle of 90°. In this way, the transmission direction of the driven gear 343 is perpendicular to the transmission direction of the driving gear 342 and is consistent with the swinging direction required by the energy conversion element 220 after the force is transmission through the engagement between the driving gear 342 and the driven gear 343.

Figure 8:
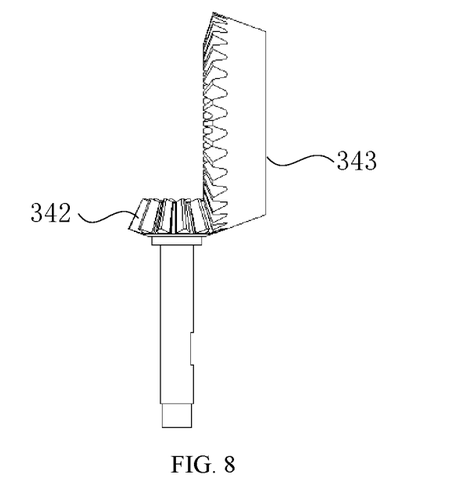
FIG. 8 is a structural schematic view of a partial gear transmission mechanism of a detection probe according to some embodiments of the present disclosure.
Figure 9:
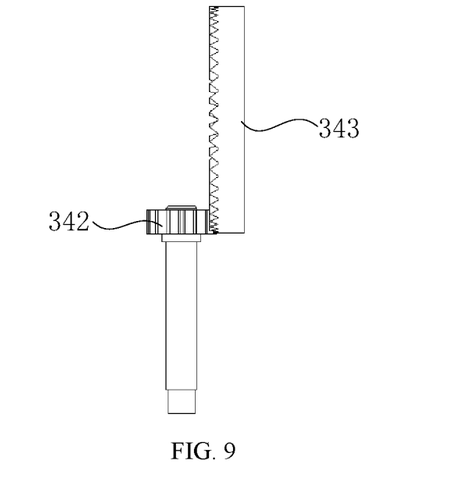
FIG. 9 is a structural schematic view of a partial gear transmission mechanism of a detection probe according to some embodiments of the present disclosure.

In some embodiments, as shown in FIG. 8, the driving gear 342 and the driven gear 343 may be bevel gears engaged with each other. In some embodiments, as shown in FIG. 9, the driving gear 342 may be a face gear, and the driven gear 343 may be a cylindrical gear, providing that the two gears may change the transmission direction, which are not limited.

In some embodiments, the first bearing 345 and the second bearing 346 are rotatably sleeved on a periphery of the driven shaft 344, are spaced apart from each other, and are arranged on the first assembly position 6121 and the second assembly position 6131 respectively, such that the driven shaft 344 is arranged on the first supporting bracket 612 and the second supporting bracket 613, and is configured to support a rotation of the driven shaft 344.

The fasten member 348 may be sleeved on the periphery of a driven shaft 344 and be arranged on one side of the driven gear 343 to cooperate with the driven shaft 344 to fix the driven gear 343, thereby avoiding axial movement of the driven gear 343 during operation and improving a transmission stability of the gear transmission mechanism 340. In some embodiments, the fasten member 348 may be a snap spring or other member capable of playing a role mentioned above.

In some embodiments, the driven shaft 344 may be connected to the rope transmission mechanism 350 to output the force received by the driving shaft 341 to the rope transmission mechanism 350. In some embodiments, as shown FIGS. 5 and 6, the rope transmission mechanism 350 may include a rope wheel 351, a rope set 352, a tension member 353, a rope wheel shaft, and the like.

In some embodiments, the rope wheel shaft may be connected to the output end of the gear transmission mechanism 340 to receive the force from the gear transmission mechanism 340 and rotate with the gear transmission mechanism 340. It should be noted that, in this embodiment, the rope wheel shaft is the driven shaft 344 of the gear transmission mechanism, in other words, the rope wheel shaft is the output end of the gear trans mission mechanism 340 and the input end of the rope transmission mechanism 350.

In some embodiments, the rope wheel 351 may be arranged on the periphery of the driven shaft 344 and spaced apart from the driven gear 343. In some embodiments, the rope wheel 351 may be arranged on one side of the second supporting bracket 613 away from the first supporting bracket 612, and may be connected to the driven shaft 344 through a flat key 354, so as to rotate under a drive of the driven shaft 344.

Figure 10:
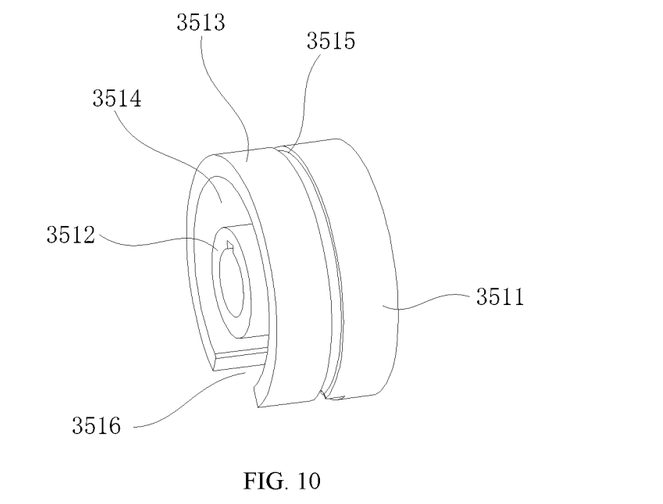
FIG. 10 is a structural schematic view of a rope wheel of a detection probe according to some embodiments of the present disclosure.

In some embodiments, as shown in FIG. 10, the rope wheel 351 may include a rope wheel body 3511, a shaft sleeve 3512, and an outer flange 3513. The rope wheel body 3511 is a body structure of the rope wheel 351, and is sleeved on the periphery of the driven shaft 344. The shaft sleeve 3512 is connected to one side of the rope wheel body 3511, extends along an axial direction of the rope wheel body 3511, and is sleeved on the periphery of the driven shaft 344. The outer flange 3513 is arranged around a periphery of the rope wheel body 3511 and extends along the axial direction of the rope wheel body 3511.

The outer flange 3513 together with the rope wheel body 3511 and the shaft sleeve 3512 defines a receiving groove 3514 around a periphery of the shaft sleeve 3512, and the outer flange 3513 defines a concave guide groove 3515 arranged around a periphery of the guide groove 3515, and a gap 3516 in communication with the receiving groove 3514 and the guide groove 3515.

In some embodiments, the receiving groove 3514 may be in a shape of at least partial annular, and may be arranged on one side along the axial direction of the rope wheel body 3511. The gap 3516 may be arranged on the rope wheel 351 close to the assembly base body 611.

Figure 11:
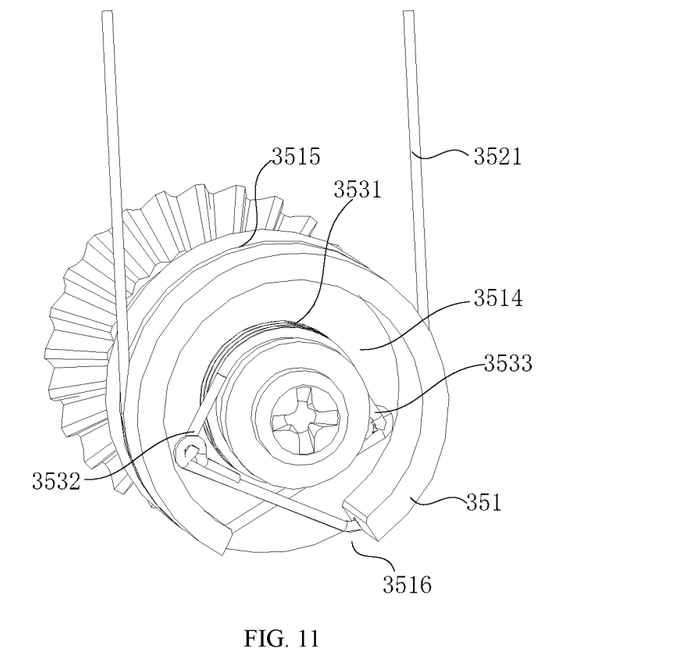
FIG. 11 is a structural schematic view of a partial transmission apparatus of a detection probe according to some embodiments of the present disclosure.

In some embodiments, as shown in FIG. 11, the tension member 353 may be arranged in the receiving groove 3514, and may include a force applying portion 3531, a first connection end 3532 and a second connection end 3533 respectively connected to two ends of the force applying portion 3531. The force applying portion 3531 is sleeved on the periphery of the shaft sleeve 3512, and may be limited by a spacer 355, and a cheese head screw 356, etc. The spacer 355 and the cheese head screw 356 are arranged at an end of the driven shaft 244 close to the rope wheel 351.

The rope set 352 may be arranged around the periphery of the rope wheel 351 and configured to move under a drive of the rope wheel 351. In some embodiments, the rope set 352 may include two ropes 3521, and first ends of the two ropes 3521 away from the tension member 353 may be respectively arranged in corresponding assembly grooves 232 of the mounting base 230 to drive the energy conversion element 220 to move through the mounting base 230. Second ends of the two ropes 3521 away from the first ends are arranged around the guide grooves 3515 of the rope wheel 351 to move with a rotation of the rope wheel 351. The two ropes 3521 may enter the receiving groove 3514 through a gap 3516 along the guide groove 3515, and are connected to a first connection end 3532 and a second connection end 3533 respectively, so as to apply a pulling force along a direction away from the detection mechanism 200 to the second end of the corresponding rope 3521 under an action of the force applying part 3531, thereby enabling the corresponding rope 3521 to be in a tension state. In this way, the rope transmission mechanism 350 drives the energy conversion element 220 to stably swing, such that the detection probe 1000 may stably scan and detect, thereby improving an accuracy of the detection result.

In some embodiments, the tension member 353 may be an elastic member, such as a spring including a torsion spring or the like. The force applying portion 3531 may elastically deform to generate an elastic force to apply a pulling force to the corresponding rope 3521 through the first connection end 3532 and the second connection end 3533, so as to enable the corresponding rope 3521 to be in the tension state.

It should be noted that, in some embodiments, the tension member 353 is connected to ends of the two ropes 3521 away from the detection mechanism 200, and is configured to apply a force to the ends, so as to enable the two ropes 3521 to be in the tension state.

It should also be noted that, in some embodiments, the transmission apparatus 300 is not limited to the above structures. For example, in an application scenario, the assembly base 610 and the like in the mounting assembly 600 may also be a part of the transmission apparatus 300. In another application scenario, the transmission apparatus 300 may also not include the shaft coupling 360 and the like, which may be arranged according to a practical situation, and is not limited.

In some embodiments, as shown in FIGS. 3, 5 and 6, the mounting assembly 600 may include an assembly bracket 630. The assembly bracket 630 may be arranged on one side of the assembly base body 611 away from the first supporting bracket 612 and the second supporting bracket 613. The driving mechanism 400 may be arranged on the assembly bracket 630.

In some embodiments, the driving mechanism 400 may be a motor, such as a stepping motor. In response to being operated, the driving mechanism 400 may output a force through the output end, and transmit the force to the gear mechanism 340 through a connection between the shaft coupling 360 and the driving shaft 341 of the gear mechanism 340.

In some embodiments, as shown in FIGS. 1 to 3, the tail sleeve assembly 500 may include a circuit structure configured for the detection probe 1000 to work. The host 2000 may be connected to the detection mechanism 200, the driving mechanism 400 and the like of the detection probe 1000 by connecting to the circuit in the tail sleeve assembly 500, thereby implementing signal control and transmission of power and data.

A detection probe is provided and includes a housing, a detection mechanism, a driving mechanism, and a rope transmission mechanism. The housing defines an accommodation space. The detection mechanism is arranged on one end of the housing, and is configured to perform a detection function. The driving mechanism is arranged in the accommodation space, and is configured to output a force. The rope transmission mechanism is arranged in the accommodation space, and includes a rope set and a tension member. One end of the rope set is connected to the driving mechanism, and other end of the rope set is connected to the detection mechanism. The rope set is configured to receive the force output by the driving mechanism, transmit the force to the detection mechanism, and drive the detection mechanism to move. The tension member is connected to the rope set, is configured to apply a force to one end of the rope set away from the detection mechanism and enable the rope set to be in a tension state.

In some embodiments, the rope set includes two ropes, a first end of each of the ropes is connected to the detection mechanism, and the tension member includes a force applying portion, a first connection end and a second connection end. The first connection end and the second connection end are arranged on two ends of the force applying portion respectively, are connected to second ends of the two ropes respectively, are configured to apply a pulling force along a direction away from the detection mechanism to the second end of the corresponding rope under an action of the force applying portion, and are configured to enable the corresponding rope to be in the tension state.

In some embodiments, the force applying portion is an elastic force applying portion configured to elastically deform to generate an elastic force, and is configured to apply the pulling force to the corresponding rope through the first connection end and the second connection end under the elastic force, and enable the corresponding rope to be in the tension state.

In some embodiments, the rope transmission mechanism further includes a rope wheel shaft and a rope wheel. The rope wheel shaft is connected to the driving mechanism, and is configured to receive the force output by the driving mechanism to rotate. The rope wheel is sleeved on a periphery of the rope wheel shaft, and is configured to rotate with the rope wheel shaft. Each of the ropes is arranged around a periphery of the rope wheel and is configured to drive the detection mechanism to move with a rotation of the rope wheel. The tension member is a torsional elastic member, and the force applying portion is sleeved on the periphery of the rope wheel shaft.

In some embodiments, the rope wheel includes a rope wheel body and a shaft sleeve. The rope wheel body is sleeved on the periphery of the rope wheel shaft. The shaft sleeve is connected to one side of the rope wheel body, extends along an axial direction of the rope wheel body, and is sleeved on the periphery of the rope wheel shaft. The force applying portion is sleeved on a periphery of the shaft sleeve.

In some embodiments, the rope wheel further includes an outer flange. The outer flange is arranged around a periphery of the rope wheel body, extends along the axial direction of the rope wheel body, jointly define a receiving groove arranged around the periphery of the shaft sleeve with the rope wheel body and the shaft sleeve, and has a gap in communication with the receiving groove. The tension member is accommodated in the receiving groove; the second ends of the two ropes enter the receiving groove through the gap along the periphery of the rope wheel, and are connected to the first connection end and the second connection end respectively.

In some embodiments, the outer flange further defines a concave guide groove arranged around a periphery of the outer flange; the guide groove is communication with the receiving groove through the gap, and the two ropes are respectively arranged around the guide groove and enter the receiving groove through the gap to connect to the tension member.

In some embodiments, the detection probe includes a gear transmission mechanism arranged in the accommodation space, connected to the driving mechanism and the rope transmission mechanism respectively, and configured to receive the force output by the driving mechanism and transmit the force to the rope transmission mechanism.

In some embodiments, the gear transmission mechanism includes a driving shaft, a driving gear, a driven gear, and a driven shaft. The driving shaft is connected to the driving mechanism, and is configured to rotate under a drive of the driving mechanism. The driving gear is connected to the driving shaft, and is configured to rotate synchronously with the driving shaft. The driven gear is engaged with the driving gear, and is configured to rotate with the driving gear. The driven shaft is connected to the driven gear, is configured to rotate synchronously with the driven gear, is connected to the rope transmission mechanism, and is configured to transmit power to the rope transmission mechanism.

In some embodiments, an axis of the driving shaft and an axis of the driven shaft form a preset angle, the preset angle is greater than 0° and not greater than 90°.

In some embodiments, the preset angle is 90°.

In some embodiments, he driving gear and the driven gear are bevel gears; or the driving gear is face gear, and the driven gear is cylindrical gear.

In some embodiments, a transmission ratio of the driving gear to the driven gear is greater than 1.

In some embodiments, the rope transmission mechanism further includes a rope wheel, arranged on a periphery of the driven shaft, spaced apart from the driven gear, and configured to rotate with the driven shaft. The rope set is arranged around a periphery of the rope wheel, and configured to drive the detection mechanism to move with a rotation of the rope wheel.

In some embodiments, the detection probe includes an assembly base, arranged on the housing and surrounded by an inner side wall of the housing, and defining an assembly hole extending through the assembly base. One end of the driving shaft is connected to the driving gear, and other end of the driving shaft penetrates the assembly hole and is connected to the driving mechanism, and the driven shaft is rotatably arranged on the assembly base.

In some embodiments, the assembly base includes: an assembly base body, arranged on the housing and surrounded by the inner side wall of the housing, and defining the assembly hole; a first supporting bracket and a second supporting bracket, respectively arranged on two sides of the assembly hole and spaced apart from each other, connected to one side of the assembly base, and respectively defining a first assembly position and a second assembly position; the gear transmission mechanism further includes a first bearing and a second bearing, the first bearing and the second bearing are arranged in the first assembly position and the second assembly position respectively, and are rotatably sleeved on a periphery of the driven shaft.

In some embodiments, the detection probe includes an assembly bracket, arranged on one side of the assembly base body away from the first supporting bracket and the second supporting bracket; the driving mechanism is arranged on the assembly bracket.

In some embodiments, the detection probe includes a shaft coupling, one end of the shaft coupling being connected to the driving mechanism, other end of the shaft coupling being connected to the driving shaft, and the shaft coupling being configured to transmit the force output by the driving mechanism to the driving shaft.

In some embodiments, an end of the housing close to the detection mechanism defines an opening in communication with the accommodation space, and the detection mechanism includes: an energy conversion element, configured to transmit a detection signal and receive a feedback signal carrying detection information; a supporting bracket, arranged on the housing at the opening, and including two concave arc supporting platforms; an mounting base, defining an assembly position to assemble the energy conversion element, connected to the rope set, and including two cylindrical protrusions respectively arranged on two sides of the mounting base; the two cylindrical protrusions are movably supported on corresponding concave arc supporting platforms respectively, and are configured to drive the energy conversion element to perform reciprocating swing under an action of the rope set; and an acoustic window, arranged on a periphery of the energy conversion element, the supporting bracket and the mounting base, arranged on the opening of the housing, and configured to cooperate with the energy conversion element to transmit the detection signal and receive the feedback signal.

In some embodiments, assembly grooves are defined on two sides of the mounting base, the rope set includes two ropes, and ends of the two ropes away from the tension member are arranged in corresponding assembly grooves respectively.

In some embodiments, the accommodation space includes an extension region and an accommodation region, and the housing includes: an insertion portion, corresponding to the extension region, at least a part of the rope transmission mechanism is accommodated in the extension region; and a holding portion, connected to one end of the insertion portion, and corresponding to the accommodation region, the driving mechanism is accommodated in the accommodation region.

A transmission apparatus is provided and arranged in a detection probe including a detection mechanism and a driving mechanism, and the transmission apparatus includes a rope set, one end of the rope set being connected to the driving mechanism, other end of the rope set being connected to the detection mechanism, the rope set being configured to receive a force output by the driving mechanism, transmit the force to the detection mechanism, and drive the detection mechanism to move; and a tension member, connected to the rope set, configured to apply a force to an end of the rope set away from the detection mechanism and enable the rope set to be in a tension state.

A detection device is provided and includes a host and any one of the detection probes mentioned above. The host is connected to the detection mechanism and the driving mechanism of the detection probe, and is configured to control of the driving mechanism to output a force and control the detection mechanism to perform a detection function.

The above is only some embodiments of the present disclosure, but the scope of the present disclosure is not limited thereto. Within the technical scope disclosed by the present disclosure, an equivalent substitution or modification made by those skilled in the art according to the technical solutions of the present disclosure and the inventive concept thereof shall be covered by the scope of the present disclosure. Furthermore, although certain terms are used in this specification, these terms are for convenience only and do not constitute any limitation to the present disclosure.

What is claimed is:

1. A detection probe, comprising:
   a housing, defining an accommodation space;
   a detection mechanism, arranged on one end of the housing, and configured to perform a detection function;
   a driving mechanism, arranged in the accommodation space, and configured to output a force; and
   a rope transmission mechanism, arranged in the accommodation space, and comprising:
      a rope set, one end of the rope set being connected to the driving mechanism, other end of the rope set being connected to the detection mechanism, the rope set being configured to receive the force output by the driving mechanism, transmit the force to the detection mechanism, and drive the detection mechanism to move; and
      a tension member, connected to the rope set, and configured to apply a force to one end of the rope set away from the detection mechanism and enable the rope set to be in a tension state;
   wherein the rope set comprises two ropes, a first end of each of the ropes is connected to the detection mechanism, and the tension member comprises:
   a force applying portion; and
   a first connection end and a second connection end, arranged on two ends of the force applying portion respectively, connected to second ends of the two ropes respectively, and configured to apply a pulling force along a direction away from the detection mechanism to the second end of the corresponding rope under an action of the force applying portion, and configured to enable the corresponding rope to be in the tension state;
   wherein the rope transmission mechanism further comprises:
   a rope wheel shaft, connected to the driving mechanism, and configured to receive the force output by the driving mechanism to rotate; and
   a rope wheel, sleeved on a periphery of the rope wheel shaft, and configured to rotate with the rope wheel shaft, wherein each of the ropes is arranged around a periphery of the rope wheel and is configured to drive the detection mechanism to move with a rotation of the rope wheel;
   wherein the rope wheel comprises:
   a rope wheel body, sleeved on the periphery of the rope wheel shaft;
   a shaft sleeve, connected to one side of the rope wheel body, extending along an axial direction of the rope wheel body, and sleeved on the periphery of the rope wheel shaft; and
   an outer flange, arranged around a periphery of the rope wheel body, extending along the axial direction of the rope wheel body, jointly defining a receiving groove arranged around the periphery of the shaft sleeve with the rope wheel body and the shaft sleeve, and having a gap in communication with the receiving groove;
   wherein the tension member is accommodated in the receiving groove; the second ends of the two ropes enter the receiving groove through the gap along the periphery of the rope wheel, and are connected to the first connection end and the second connection end respectively;
   wherein the outer flange further defines a concave guide groove arranged around a periphery of the outer flange; wherein the guide groove is communication with the receiving groove through the gap, and the two ropes are respectively arranged around the guide groove and enter the receiving groove through the gap to connect to the tension member.

2. The detection probe as claimed in claim 1, wherein the force applying portion is an elastic force applying portion configured to elastically deform to generate an elastic force, and is configured to apply the pulling force to the corresponding rope through the first connection end and the second connection end under the elastic force, and enable the corresponding rope to be in the tension state.

3. The detection probe as claimed in claim 1,
   wherein the tension member is a torsional elastic member, and the force applying portion is sleeved on the periphery of the rope wheel shaft.

4. The detection probe as claimed in claim 3,
   wherein the force applying portion is sleeved on a periphery of the shaft sleeve.

5. The detection probe as claimed in claim 1, further comprising:
   a gear transmission mechanism, arranged in the accommodation space, connected to the driving mechanism and the rope transmission mechanism respectively, and configured to receive the force output by the driving mechanism and transmit the force to the rope transmission mechanism.

6. The detection probe as claimed in claim 5, wherein the gear transmission mechanism comprises:
   a driving shaft, connected to the driving mechanism, and configured to rotate under a drive of the driving mechanism;
   a driving gear, connected to the driving shaft, and configured to rotate synchronously with the driving shaft;
   a driven gear, engaged with the driving gear, and configured to rotate with the driving gear; and
   a driven shaft, connected to the driven gear, configured to rotate synchronously with the driven gear, connected to the rope transmission mechanism, and configured to transmit power to the rope transmission mechanism.

7. The detection probe as claimed in claim 6, wherein an axis of the driving shaft and an axis of the driven shaft form a preset angle, the preset angle is greater than 0° and not greater than 90°.

8. The detection probe as claimed in claim 6, wherein the driving gear and the driven gear are bevel gears; or the driving gear is face gear, and the driven gear is cylindrical gear; or
   a transmission ratio of the driving gear to the driven gear is greater than 1; or
   the rope transmission mechanism further comprises: a rope wheel, arranged on a periphery of the driven shaft, spaced apart from the driven gear, and configured to rotate with the driven shaft; wherein the rope set is arranged around a periphery of the rope wheel, and configured to drive the detection mechanism to move with a rotation of the rope wheel.

9. The detection probe as claimed in claim 6, further comprising:
   an assembly base, arranged on the housing and surrounded by an inner side wall of the housing, and defining an assembly hole extending through the assembly base;
   wherein one end of the driving shaft is connected to the driving gear, and other end of the driving shaft penetrates the assembly hole and is connected to the driving mechanism, and the driven shaft is rotatably arranged on the assembly base.

10. The detection probe as claimed in claim 9, wherein the assembly base comprises:
- an assembly base body, arranged on the housing and surrounded by the inner side wall of the housing, and defining the assembly hole;
- a first supporting bracket and a second supporting bracket, respectively arranged on two sides of the assembly hole and spaced apart from each other, connected to one side of the assembly base, and respectively defining a first assembly position and a second assembly position;
- wherein the gear transmission mechanism further comprises a first bearing and a second bearing, the first bearing and the second bearing are arranged in the first assembly position and the second assembly position respectively, and are rotatably sleeved on a periphery of the driven shaft.

11. The detection probe as claimed in claim 10, further comprising:
- an assembly bracket, arranged on one side of the assembly base body away from the first supporting bracket and the second supporting bracket;
- wherein the driving mechanism is arranged on the assembly bracket.

12. The detection probe as claimed in claim 6, further comprising:
- a shaft coupling, one end of the shaft coupling being connected to the driving mechanism, other end of the shaft coupling being connected to the driving shaft, and the shaft coupling being configured to transmit the force output by the driving mechanism to the driving shaft.

13. The detection probe as claimed in claim 1, wherein an end of the housing close to the detection mechanism defines an opening in communication with the accommodation space, and the detection mechanism comprises:
- an energy conversion element, configured to transmit a detection signal and receive a feedback signal carrying detection information;
- a supporting bracket, arranged on the housing at the opening, and comprising two concave arc supporting platforms;
- a mounting base, defining an assembly position to assemble the energy conversion element, connected to the rope set, and comprising two cylindrical protrusions respectively arranged on two sides of the mounting base; wherein the two cylindrical protrusions are movably supported on corresponding concave arc supporting platforms respectively, and are configured to drive the energy conversion element to perform reciprocating swing under an action of the rope set; and
- an acoustic window, arranged on a periphery of the energy conversion element, the supporting bracket and the mounting base, arranged on the opening of the housing, and configured to cooperate with the energy conversion element to transmit the detection signal and receive the feedback signal.

14. The detection probe as claimed in claim 13, wherein assembly grooves are defined on two sides of the mounting base, the rope set comprises two ropes, and ends of the two ropes away from the tension member are arranged in corresponding assembly grooves respectively.

15. The detection probe as claimed in claim 1, wherein the accommodation space comprises an extension region and an accommodation region, and the housing comprises:
- an insertion portion, corresponding to the extension region, wherein at least a part of the rope transmission mechanism is accommodated in the extension region; and
- a holding portion, connected to one end of the insertion portion, and corresponding to the accommodation region, wherein the driving mechanism is accommodated in the accommodation region.

16. A transmission apparatus, arranged in a detection probe comprising a detection mechanism and a driving mechanism, and the transmission apparatus comprising a rope transmission mechanism comprising:
- a rope set, one end of the rope set being connected to the driving mechanism, other end of the rope set being connected to the detection mechanism, the rope set being configured to receive a force output by the driving mechanism, transmit the force to the detection mechanism, and drive the detection mechanism to move; and
- a tension member, connected to the rope set, configured to apply a force to an end of the rope set away from the detection mechanism and enable the rope set to be in a tension state;
- wherein the rope set comprises two ropes, a first end of each of the ropes is connected to the detection mechanism, and the tension member comprises:
- a force applying portion; and
- a first connection end and a second connection end, arranged on two ends of the force applying portion respectively, connected to second ends of the two ropes respectively, and configured to apply a pulling force along a direction away from the detection mechanism to the second end of the corresponding rope under an action of the force applying portion, and configured to enable the corresponding rope to be in the tension state;
- wherein the rope transmission mechanism further comprises:
- a rope wheel shaft, connected to the driving mechanism, and configured to receive the force output by the driving mechanism to rotate; and
- a rope wheel, sleeved on a periphery of the rope wheel shaft, and configured to rotate with the rope wheel shaft, wherein each of the ropes is arranged around a periphery of the rope wheel and is configured to drive the detection mechanism to move with a rotation of the rope wheel;
- wherein the rope wheel comprises:
- a rope wheel body, sleeved on the periphery of the rope wheel shaft;
- a shaft sleeve, connected to one side of the rope wheel body, extending along an axial direction of the rope wheel body, and sleeved on the periphery of the rope wheel shaft; and
- an outer flange, arranged around a periphery of the rope wheel body, extending along the axial direction of the rope wheel body, jointly defining a receiving groove arranged around the periphery of the shaft sleeve with the rope wheel body and the shaft sleeve, and having a gap in communication with the receiving groove;
- wherein the tension member is accommodated in the receiving groove; the second ends of the two ropes enter the receiving groove through the gap along the periphery of the rope wheel, and are connected to the first connection end and the second connection end respectively;
- wherein the outer flange further defines a concave guide groove arranged around a periphery of the outer flange;

wherein the guide groove is communication with the receiving groove through the gap, and the two ropes are respectively arranged around the guide groove and enter the receiving groove through the gap to connect to the tension member.

17. A detection device, comprising:
a host; and
a detection probe comprising:
  a housing, defining an accommodation space;
  a detection mechanism, arranged on one end of the housing, and configured to perform a detection function;
  a driving mechanism, arranged in the accommodation space, and configured to output a force; and
  a rope transmission mechanism, arranged in the accommodation space, and comprising:
    a rope set, one end of the rope set being connected to the driving mechanism, other end of the rope set being connected to the detection mechanism, the rope set being configured to receive the force output by the driving mechanism, transmit the force to the detection mechanism, and drive the detection mechanism to move; and
    a tension member, connected to the rope set, and configured to apply a force to one end of the rope set away from the detection mechanism and enable the rope set to be in a tension state;
wherein the host is connected to the detection mechanism and the driving mechanism of the detection probe, and is configured to control of the driving mechanism to output the force and control the detection mechanism to perform a detection function;
wherein the rope set comprises two ropes, a first end of each of the ropes is connected to the detection mechanism, and the tension member comprises:
a force applying portion; and
a first connection end and a second connection end, arranged on two ends of the force applying portion respectively, connected to second ends of the two ropes respectively, and configured to apply a pulling force along a direction away from the detection mechanism to the second end of the corresponding rope under an action of the force applying portion, and configured to enable the corresponding rope to be in the tension state;
wherein the rope transmission mechanism further comprises:
a rope wheel shaft, connected to the driving mechanism, and configured to receive the force output by the driving mechanism to rotate; and
a rope wheel, sleeved on a periphery of the rope wheel shaft, and configured to rotate with the rope wheel shaft, wherein each of the ropes is arranged around a periphery of the rope wheel and is configured to drive the detection mechanism to move with a rotation of the rope wheel;
wherein the rope wheel comprises:
a rope wheel body, sleeved on the periphery of the rope wheel shaft;
a shaft sleeve, connected to one side of the rope wheel body, extending along an axial direction of the rope wheel body, and sleeved on the periphery of the rope wheel shaft; and
an outer flange, arranged around a periphery of the rope wheel body, extending along the axial direction of the rope wheel body, jointly defining a receiving groove arranged around the periphery of the shaft sleeve with the rope wheel body and the shaft sleeve, and having a gap in communication with the receiving groove;
wherein the tension member is accommodated in the receiving groove; the second ends of the two ropes enter the receiving groove through the gap along the periphery of the rope wheel, and are connected to the first connection end and the second connection end respectively;
wherein the outer flange further defines a concave guide groove arranged around a periphery of the outer flange; wherein the guide groove is communication with the receiving groove through the gap, and the two ropes are respectively arranged around the guide groove and enter the receiving groove through the gap to connect to the tension member.

18. The detection probe as claimed in claim 6, wherein the force applying portion is sleeved on the periphery of the shaft sleeve and is limited by a spacer and a cheese head screw, the spacer and the cheese head screw are arranged at an end of the driven shaft close to the rope wheel.

19. The transmission apparatus as claimed in claim 16, wherein the transmission apparatus further comprises: a gear transmission mechanism, arranged in a accommodation space, connected to the driving mechanism and the rope transmission mechanism respectively, and configured to receive the force output by the driving mechanism and transmit the force to the rope transmission mechanism;
  wherein the gear transmission mechanism comprises:
    a driving shaft, connected to the driving mechanism, and configured to rotate under a drive of the driving mechanism;
    a driving gear, connected to the driving shaft, and configured to rotate synchronously with the driving shaft;
    a driven gear, engaged with the driving gear, and configured to rotate with the driving gear; and
    a driven shaft, connected to the driven gear, configured to rotate synchronously with the driven gear, connected to the rope transmission mechanism, and configured to transmit power to the rope transmission mechanism;
  wherein the force applying portion is sleeved on the periphery of the shaft sleeve and is limited by a spacer and a cheese head screw, the spacer and the cheese head screw are arranged at an end of the driven shaft close to the rope wheel.

20. The detection device as claimed in claim 17, wherein the detection probe further comprises: a gear transmission mechanism, arranged in the accommodation space, connected to the driving mechanism and the rope transmission mechanism respectively, and configured to receive the force output by the driving mechanism and transmit the force to the rope transmission mechanism;
  wherein the gear transmission mechanism comprises:
    a driving shaft, connected to the driving mechanism, and configured to rotate under a drive of the driving mechanism;
    a driving gear, connected to the driving shaft, and configured to rotate synchronously with the driving shaft;
    a driven gear, engaged with the driving gear, and configured to rotate with the driving gear; and
    a driven shaft, connected to the driven gear, configured to rotate synchronously with the driven gear, connected to the rope transmission mechanism, and configured to transmit power to the rope transmission mechanism;
  wherein the force applying portion is sleeved on the periphery of the shaft sleeve and is limited by a spacer and a cheese head screw, the spacer and the cheese head screw are arranged at an end of the driven shaft close to the rope wheel.

\* \* \* \* \*